US010988442B2

(12) United States Patent
Fung et al.

(10) Patent No.: US 10,988,442 B2
(45) Date of Patent: Apr. 27, 2021

(54) NITRITE SALTS OF 1,1-DIMETHYLBIGUANIDE, PHARMACEUTICAL COMPOSITIONS, AND METHODS OF USE

(71) Applicant: NovoMedix, LLC, San Diego, CA (US)

(72) Inventors: Leah M. Fung, San Diego, CA (US); Kyle W. H. Chan, San Diego, CA (US); Robert W. Sullivan, Vista, CA (US); Cathy A. Swindlehurst, San Diego, CA (US)

(73) Assignee: NovoMedix, LLC, San Diego, CA (US)

( * ) Notice: Subject to any disclaimer, the term of this patent is extended or adjusted under 35 U.S.C. 154(b) by 222 days.

(21) Appl. No.: 15/806,952

(22) Filed: Nov. 8, 2017

(65) Prior Publication Data

US 2018/0127359 A1 May 10, 2018

Related U.S. Application Data

(60) Provisional application No. 62/419,892, filed on Nov. 9, 2016.

(51) Int. Cl.

| | | |
|---|---|---|
| *C07C 279/04* | (2006.01) | |
| *A61K 31/426* | (2006.01) | |
| *A61K 31/427* | (2006.01) | |
| *A61K 31/702* | (2006.01) | |
| *A61K 31/70* | (2006.01) | |
| *A61K 31/4985* | (2006.01) | |
| *A61K 31/522* | (2006.01) | |
| *A61K 31/64* | (2006.01) | |
| *A61K 38/26* | (2006.01) | |
| *A61K 31/4439* | (2006.01) | |
| *A61P 9/00* | (2006.01) | |
| *A61P 3/10* | (2006.01) | |
| *A61P 9/12* | (2006.01) | |
| *A61K 9/28* | (2006.01) | |
| *A61K 31/155* | (2006.01) | |
| *A61K 45/06* | (2006.01) | |

(52) U.S. Cl.
CPC .............. *C07C 279/04* (2013.01); *A61K 9/28* (2013.01); *A61K 31/155* (2013.01); *A61K 31/426* (2013.01); *A61K 31/427* (2013.01); *A61K 31/4439* (2013.01); *A61K 31/4985* (2013.01); *A61K 31/522* (2013.01); *A61K 31/64* (2013.01); *A61K 31/70* (2013.01); *A61K 31/702* (2013.01); *A61K 38/26* (2013.01); *A61K 45/06* (2013.01); *A61P 3/10* (2018.01); *A61P 9/00* (2018.01); *A61P 9/12* (2018.01); *C07B 2200/13* (2013.01)

(58) Field of Classification Search
CPC ...... A61P 9/00; A61P 9/12; A61P 3/10; A61K 9/28
See application file for complete search history.

(56) References Cited

U.S. PATENT DOCUMENTS

| | | | | |
|---|---|---|---|---|
| 5,880,116 | A | * | 3/1999 | Vigo-Pelfrey ......... A61K 31/12 514/168 |
| 2010/0062059 | A1 | | 3/2010 | Ganzarolli De Oliveira |
| 2014/0127329 | A1 | * | 5/2014 | Giordano ............... A61K 31/13 424/718 |

FOREIGN PATENT DOCUMENTS

EP     3025707     *  6/2016

OTHER PUBLICATIONS

Lai et al., Circulation, Feb. 23, 2016, 133(8), 717-731.*
Berge et al., "Pharmaceutical salts," J. Pharm. Sci. 1977, 66, 1-19.
Fridrichova et al., "1,1-Dimethyl-biguanidium(2+) dinitrate," Acta Cryst. 2012, E68, o18-o19.
Giovannucci et al., "Diabetes and cancer: a consensus report," Diabetes Care 2010, 33, 1674-1685.
Global Report on Diabetes—World Health Organization 2016.
Go et al., "Heart disease and stroke statistics—2013 update: a report from the American Heart Association," Circulation 2013, 127, e6-e245.
Lai et al., "SIRT3-AMP-Activated Protein Kinase Activation by Nitrite and Metformin Improves Hyperglycemia and Normalizes Pulmonary Hypertension Associated With Heart Failure With Preserved Ejection Fraction," Circulation 2016, 133, 717-731.
Mendis et al., Global Atlas on Cardiovascular Disease Prevention and Control—World Health Organization, World Heart Federation, and World Stroke Organization 2011.
Naghavi et al., "Global, regional, and national age-sex specific all-cause and cause-specific mortality for 240 causes of death, 1990-2013: a systematic analysis for the Global Burden of Disease Study 2013," Lancet 2014, 385, 117-171.
Viollet et al., "Cellular and molecular mechanisms of metformin: an overview," Clin. Sci. (Lond.) 2012, 122, 253-270.
Wong et al., "Diabetes and risk of physical disability in adults: a systematic review and meta-analysis," Lancet Diabetes Endocrinol. 2013, 1, 106-114.
Brambilla et al., 2007, "Genotoxic and carcinogenic risk to humans of drug-nitrite interaction products," Mutation Research, 635(1):17-52.
Martelli et al., 2012, "Arylamine drugs: genotoxic-carcinogenic activity of NO-derivatives," Frontiers in Bioscience, E4:2071-2084.
Rao, 1980, "N-Nitrosamines from drugs and nitrite: potential source of chemical carcinogens in humans?" Phar. Inter., 1:187-190.

* cited by examiner

*Primary Examiner* — Genevieve S Alley
(74) *Attorney, Agent, or Firm* — Jones Day

(57) ABSTRACT

Provided herein are nitrite salts of 1,1-dimethylbiguanide; and isotopic variants thereof; and pharmaceutically acceptable hydrates and solvates thereof. Also provided herein are their pharmaceutical compositions and methods of use for treating, preventing, or ameliorating one or more symptoms of diseases associated with and/or caused by an abnormal blood glucose level. Further provided herein are methods of their use for treating, preventing, or ameliorating one or more symptoms of a cardiovascular disease.

30 Claims, No Drawings

NITRITE SALTS OF 1,1-DIMETHYLBIGUANIDE, PHARMACEUTICAL COMPOSITIONS, AND METHODS OF USE

CROSS REFERENCE TO RELATED APPLICATION

This application claims the benefit of U.S. Provisional Application No. 62/419,892, filed Nov. 9, 2016; the disclosure of which is incorporated herein by reference in its entirety.

FIELD

Provided herein are nitrite salts of 1,1-dimethylbiguanide; and isotopic variants thereof; and pharmaceutically acceptable hydrates and solvates thereof. Also provided herein are their pharmaceutical compositions and methods of use for treating, preventing, or ameliorating one or more symptoms of diseases associated with and/or caused by an abnormal blood glucose level. Further provided herein are methods of their use for treating, preventing, or ameliorating one or more symptoms of a cardiovascular disease.

BACKGROUND

According to the World Health Organization (WHO), the global prevalence of diabetes has nearly doubled since 1980, rising from 4.7% to 8.5% in the adult population. *Global Report on Diabetes—World Health Organization* 2016. During the same period, the obesity epidemic has more than doubled between 1980 and 2014. *Obesity and Overweight Fact Sheet—World Health Organization* 2016. It was estimated that 422 million adults globally in 2014 were living with diabetes, compared to 108 million in 1980. *Global Report on Diabetes—World Health Organization* 2016. Diabetes caused 1.5 million deaths in 2012. Id. The dramatic rise in the prevalence of obesity and diabetes is associated with increased morbidity, mortality, and public health care costs worldwide. *Global Report on Diabetes—World Health Organization* 2016; *Obesity and Overweight Fact Sheet—World Health Organization* 2016.

Diabetes can affect many parts of the body and is associated with serious complications, such as heart disease and stroke, blindness, kidney failure, and lower-limb amputation. *Global Report on Diabetes—World Health Organization* 2016. When diabetes is not well managed, complications develop that threaten health and endanger life. Id. Acute complications are a significant contributor to mortality, costs and poor quality of life. Id. Over time diabetes can damage the heart, blood vessels, eyes, kidneys, and nerves, and increase the risk of heart disease and stroke. Id. Such damage can result in reduced blood flow, which, combined with nerve damage (neuropathy) in the feet, increases the chance of foot ulcers, infection, and the eventual need for limb amputation. Id. Diabetic retinopathy is an important cause of blindness and occurs as a result of long-term accumulated damage to the small blood vessels in the retina. Diabetes is also among the leading cause of kidney failure. Id. Diabetes has also been associated with increased rates of cancers, in particular, breast, colon, prostate, kidney, and pancreas cancers, and with increased rates of physical and cognitive disability. Viollet et al., *Clin. Sci.* (*Lond.*) 2012, 122, 253-270; Wong et al., *Lancet Diabetes Endocrinology* 2013, 1, 106-114; Giovannucci et al. *Diabetes Care* 2010, 33, 1674-1685.

Cardiovascular disease is a class of diseases that involve the heart or blood vessels. Mendis et al., *Global Atlas on Cardiovascular Disease Prevention and Control World Health Organization, World Heart Federation, and World Stroke Orgnaizaiton* 2011. Cardiovascular disease includes coronary artery diseases such as angina and myocardial infarction (commonly known as a heart attack), stroke, hypertensive heart disease, rheumatic heart disease, cardiomyopathy, heart arrhythmia, congenital heart disease, valvular heart disease, carditis, aortic aneurysms, peripheral artery disease, and venous thrombosis. Id.; *Lancet* 2014, 385, 117-171. Cardiovascular diseases are the leading cause of death globally. Mendis et al., *Global Atlas on Cardiovascular Disease Prevention and Control—World Health Organization, World Heart Federation, and World Stroke Orgnaizaiton* 2011. In 2013, cardiovascular diseases resulted in 17.3 million deaths (31.5%), up from 12.3 million (25.8%) in 1990. *Lancet* 2014, 385, 117-171. In the United States 11% of people between 20 and 40 have a cardiovascular disease, while 37% between 40 and 60, 71% of people between 60 and 80, and 85% of people over 80 have a cardiovascular disease. Go et al., *Circulation* 2013, 127, e6-e245.

Therefore, there is a need for an effective therapy for treating cardiovascular diseases, and diseases associated with and/or caused by an abnormal blood glucose level.

SUMMARY OF THE DISCLOSURE

Provided herein is a solid nitrite salt of 1,1-dimethylbiguanide, or an isotopic variant thereof or a pharmaceutically acceptable hydrate or solvate thereof.

Also provided herein is an isolated nitrite salt of 1,1-dimethylbiguanide, or an isotopic variant thereof; or a pharmaceutically acceptable hydrate or solvate thereof.

Additionally provided herein is a pharmaceutical composition, comprising a solid nitrite salt or an isolated nitrite salt of 1,1-dimethylbiguanide, or an isotopic variant thereof or a pharmaceutically acceptable hydrate or solvate thereof and a pharmaceutically acceptable excipient.

Further provided herein is a method of treating, preventing, or ameliorating one or more symptoms of a disease associated with and/or caused by an abnormal blood glucose level in a subject, comprising administering to the subject a therapeutically effective amount of a solid nitrite salt or an isolated nitrite salt of 1,1-dimethylbiguanide, or an isotopic variant thereof or a pharmaceutically acceptable hydrate or solvate thereof.

Provided herein is a method of treating, preventing, or ameliorating one or more symptoms of pulmonary hypertension in a subject, comprising administering to the subject a therapeutically effective amount of a solid nitrite salt or an isolated nitrite salt of 1,1-dimethylbiguanide, or an isotopic variant thereof or a pharmaceutically acceptable hydrate or solvate thereof.

Provided herein is a method of treating, preventing, or ameliorating one or more symptoms of a cardiovascular disease in a subject, comprising administering to the subject a therapeutically effective amount of a solid nitrite salt or an isolated nitrite salt of 1,1-dimethylbiguanide, or an isotopic variant thereof or a pharmaceutically acceptable hydrate or solvate thereof.

Provided herein is a method of reducing the blood glucose level in a subject, comprising administering to the subject a therapeutically effective amount of a solid nitrite salt or an isolated nitrite salt of 1,1-dimethylbiguanide, or an isotopic variant thereof; or a pharmaceutically acceptable hydrate or solvate thereof.

DETAILED DESCRIPTION

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, *Remington: The Science and Practice of Pharmacy,* 22nd ed.; Allen Ed.: Philadelphia, Pa., 2012; *Handbook of Pharmaceutical Excipients,* 7th ed.; Rowe et al., Eds.; The Pharmaceutical Press and the American Pharmaceutical Association: 2012; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder, disease, or condition. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a disorder, disease, or condition.

The term "isotopically enriched" or "isotopic variant" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen ($^1H$), deuterium ($^2H$), tritium ($^3H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an isotopically enriched compound is in a stable form, that is, non-radioactive. In certain embodiments, an isotopically enriched compound contains unnatural proportions of one or more isotopes, including, but not limited to, hydrogen ($^1H$), deuterium ($^2H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In certain embodiments, an isotopically enriched compound is in an unstable form, that is, radioactive. In certain embodiments, an isotopically enriched compound contains unnatural proportions of one or more isotopes, including, but not limited to, tritium ($^3H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$), and iodine-131 ($^{131}I$). It will be understood that, in a compound as provided herein, any hydrogen can be $^2H$, as example, or any carbon can be $^{13}C$, as example, or any nitrogen can be $^{15}N$, as example, or any oxygen can be $^{18}O$, as example, where feasible according to the judgment of one of skill.

The term "isotopic enrichment" refers to the percentage of incorporation of a less prevalent isotope (e.g., D for hydrogen) of an element at a given position in a molecule in the place of a more prevalent isotope (e.g., $^1H$ for hydrogen) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium ($^1$H), deuterium ($^2$H or D), and tritium ($^3$H), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}$C) and carbon-13 ($^{13}$C) in their natural abundances. Carbon-12 is the most common carbon isotope having a natural abundance of more than 98.89%. Carbon-13 is a less prevalent carbon isotope having a natural abundance of about 1.11%.

The term "carbon-13 enrichment" or "$^{13}$C enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%).

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single compound, including a single enantiomer, a racemic mixture, a mixture of enantiomers, or a diastereomeric mixture thereof, as determined by standard analytical methods. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an isotopic variant thereof; or a pharmaceutically acceptable hydrate or solvate thereof" has the same meaning as the phrase "an isotopic variant of the compound referenced therein; or a pharmaceutically solvate or hydrate of the compound referenced therein, or a pharmaceutically acceptable solvate or hydrate of an isotopic variant of the compound referenced therein."

Nitrite Salts of 1,1-Dimethylbiguanide

In one embodiment, provided herein is a solid nitrite salt of 1,1-dimethylbiguanide, or an isotopic variant thereof; or a pharmaceutically acceptable hydrate or solvate thereof.

In another embodiment, provided herein is an isolated nitrite salt of 1,1-dimethylbiguanide, or an isotopic variant thereof or a pharmaceutically acceptable hydrate or solvate thereof. In one embodiment, the isolated nitrite salt of 1,1-dimethylbiguanide, or an isotopic variant thereof; or a pharmaceutically acceptable hydrate or solvate thereof, is a solid.

The structure of 1,1-dimethylbiguanide is shown below. 1,1-Dimethylbiguanide is also known as metformin, 1,1-dimethylguanylguanidine, or N,N-dimethylimidodicarbonimidic diamide.

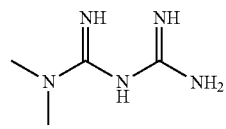

In one embodiment, the nitrite salt of 1,1-dimethylbiguanide is 1,1-dimethylbiguanide mononitrite, or an isotopic variant thereof or a pharmaceutically acceptable hydrate or solvate thereof. The structure of 1,1-dimethylbiguanide mononitrite is shown below.

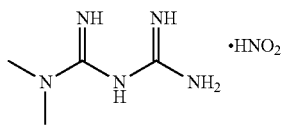

In another embodiment, the nitrite salt of 1,1-dimethylbiguanide is 1,1-dimethylbiguanide dinitrite, or an isotopic variant thereof; or a pharmaceutically acceptable hydrate or solvate thereof. The structure of 1,1-dimethylbiguanide dinitrite is shown below.

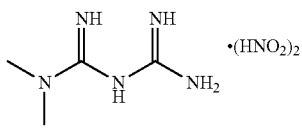

In one embodiment, the nitrite salt of 1,1-dimethylbiguanide provided herein is crystalline. In another embodiment, 1,1-dimethylbiguanide mononitrite is crystalline. In yet another embodiment, 1,1-dimethylbiguanide dinitrite is crystalline.

In one embodiment, the nitrite salt of 1,1-dimethylbiguanide provided herein is a solvate. In one embodiment, the solvent in the solvate is an alcohol. In another embodiment, the solvent in the solvate is methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, and ethyleneglycol. In yet another embodiment, the solvent in the solvate is ethanol.

In one embodiment, the nitrite salt of 1,1-dimethylbiguanide provided herein is a hydrate. In another embodiment, the nitrite salt of 1,1-dimethylbiguanide provided herein is a hemihydrate. In yet another embodiment, the nitrite salt of 1,1-dimethylbiguanide provided herein is a monohydrate. In yet another embodiment, the nitrite salt of 1,1-dimethylbiguanide provided herein is a dihydrate. In still another embodiment, the nitrite salt of 1,1-dimethylbiguanide provided herein is a trihydrate.

In one embodiment, provided herein is a composition comprises a nitrite salt of 1,1-dimethylbiguanide, or an isotopic variant thereof; or a pharmaceutically acceptable hydrate or solvate thereof; and a metal nitrite. In one embodiment, the nitrite salt is a solid nitrite salt. In another embodiment, the nitrite salt is an isolated nitrite salt.

In certain embodiments, the composition comprises no less than about 90%, no less than about 95%, no less than about 96%, no less than about 97%, no less than about 98%, no less than about 99%, no less than about 99.5%, or no less than about 99.9% of the nitrite salt of 1,1-dimethylbiguanide, or an isotopic variant thereof; or a pharmaceutically acceptable hydrate or solvate thereof. In certain embodiments, the composition comprises no less than about 90% of the nitrite salt of 1,1-dimethylbiguanide, or an isotopic variant thereof; or a pharmaceutically acceptable hydrate or solvate thereof. In certain embodiments, the composition comprises no less than about 95% of the nitrite salt of 1,1-dimethylbiguanide, or an isotopic variant thereof; or a pharmaceutically acceptable hydrate or solvate thereof. In certain embodiments, the composition comprises no less than about 98% of the nitrite salt of 1,1-dimethylbiguanide, or an isotopic variant thereof; or a pharmaceutically acceptable hydrate or solvate thereof. In certain embodiments, the composition comprises no less than about 99% of the nitrite salt of 1,1-dimethylbiguanide, or an isotopic variant thereof; or a pharmaceutically acceptable hydrate or solvate thereof.

In certain embodiments, the composition comprises no greater than about 10%, no greater than about 5%, no greater than about 4%, no greater than about 3%, no greater than about 2%, no greater than about 1%, no greater than about 0.5%, or no greater than about 0.1% of the metal nitrite. In certain embodiments, the composition comprises no greater than about 10% of the metal nitrite. In certain embodiments, the composition comprises no greater than about 5% of the metal nitrite. In certain embodiments, the composition comprises no greater than about 2% of the metal nitrite. In certain embodiments, the composition comprises no greater than about 1% of the metal nitrite.

In certain embodiments, the metal nitrite is an alkali metal nitrite. In certain embodiments, the metal nitrite is sodium nitrite. In certain embodiments, the metal nitrite is potassium nitrite. In certain embodiments, the metal nitrite is an alkaline earth metal nitrite. In certain embodiments, the metal nitrite is calcium nitrite. In certain embodiments, the metal nitrite is magnesium nitrite. In certain embodiments, the metal nitrite is silver nitrite.

Process of Preparation

In one embodiment, provided herein is a process for preparing a nitrite salt of 1,1-dimethylbiguanide provided herein, comprising the step of contacting 1,1-dimethylbiguanide with nitrous acid in a solvent at a first predetermined temperature.

In certain embodiments, the molar ratio of nitrous acid versus 1,1-dimethylbiguanide in the contacting step to form the nitrite salt of 1,1-dimethylbiguanide provided herein is about 1. In certain embodiments, the contacting step to form the nitrite salt of 1,1-dimethylbiguanide provided herein is performed in the presence of an excess amount of nitrous acid to 1,1-dimethylbiguanide to maximize the yield of the process. In certain embodiments, the molar ratio of nitrous acid versus 1,1-dimethylbiguanide is no less than about 1.01, no less than about 1.05, no less than about 1.1, or no less than about 1.2. In certain embodiments, the molar ratio of nitrous acid versus 1,1-dimethylbiguanide is ranging from about 1.05 to about 10, from about 1.1 to about 5, or from about 1.2 to about 2.5.

In another embodiment, provided herein is a process for preparing a nitrite salt of 1,1-dimethylbiguanide provided herein, comprising the step of contacting 1,1-dimethylbiguanide with a first nitrite salt in a solvent at a first predetermined temperature.

In certain embodiments, the molar ratio of the first nitrite salt versus 1,1-dimethylbiguanide in the contacting step to form the nitrite salt of 1,1-dimethylbiguanide provided herein is about 1. In certain embodiments, the contacting step to form the nitrite salt of 1,1-dimethylbiguanide provided herein is performed in the presence of an excess amount of the first nitrite salt to maximize the yield of the process. In certain embodiments, the molar ratio of the first nitrite salt versus 1,1-dimethylbiguanide is no less than about 1.01, no less than about 1.05, no less than about 1.1, or no less than about 1.2. In certain embodiments, the molar ratio of the first nitrite salt versus 1,1-dimethylbiguanide is ranging from about 1.05 to about 10, from about 1.1 to about 5, or from about 1.2 to about 2.5.

In yet another embodiment, provided herein is a process for preparing a nitrite salt of 1,1-dimethylbiguanide provided herein, comprising the step of contacting a first 1,1-dimethylbiguanide salt with a first nitrite salt in a solvent at a first predetermined temperature.

In one embodiment, the first 1,1-dimethylbiguanide salt is a hydrochloric acid, hydrobromic acid, or sulfuric acid salt of 1,1-dimethylbiguanide. In another embodiment, the first 1,1-dimethylbiguanide salt is a 1,1-dimethylbiguanide hydrochloric acid salt. In yet another embodiment, the first 1,1-dimethylbiguanide salt is 1,1-dimethylbiguanide monohydrochloride. In yet another embodiment, the first 1,1-dimethylbiguanide salt is 1,1-dimethylbiguanide dihydrochloride.

In certain embodiments, the first nitrite salt is an organic salt. In certain embodiments, the first nitrite salt is an inorganic salt. In certain embodiments, the first nitrite salt is sodium nitrite. In certain embodiments, the first nitrite salt is potassium nitrite. In certain embodiments, the first nitrite salt is magnesium nitrite. In certain embodiments, the first nitrite salt is silver nitrite.

In certain embodiments, the molar ratio of the first nitrite salt versus the first 1,1-dimethylbiguanide salt in the contacting step to form the nitrite salt of 1,1-dimethylbiguanide provided herein is about 1. In certain embodiments, the contacting step to form the nitrite salt of 1,1-dimethylbiguanide provided herein is performed in the presence of an excess amount of the first nitrite salt to maximize the yield of the process. In certain embodiments, the molar ratio of the first nitrite salt versus the first 1,1-dimethylbiguanide salt is no less than about 1.01, no less than about 1.05, no less than about 1.1, or no less than about 1.2. In certain embodiments, the molar ratio of the first nitrite salt versus the first 1,1-dimethylbiguanide salt is ranging from about 1.05 to about 10, from about 1.1 to about 5, or from about 1.2 to about 2.5.

Suitable solvents for use in the contacting step to form the nitrite salt of 1,1-dimethylbiguanide provided herein include, but are not limited to, hydrocarbons, including petroleum ether, pentane, hexane(s), heptane, octane, isooctane, cyclopentane, cyclohexane, methylcyclohexane, benzene, toluene, xylene, tetralin, and cumene; chlorinated hydrocarbons, including dichloromethane (DCM), 1,2-dichloroethane, 1,1-dichloroethene, 1,2-dichloroethene, chloroform, trichloroethane, trichloroethene, carbon tetrachloride, chlorobenzene, and trifluoromethylbenzene; alcohols, including methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, and ethyleneglycol; ethers, including diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, and anisole; ketones, including acetone, butanone, methyl ethyl ketone (MEK), methyl isopropyl ketone, methyl butyl ketone, and methyl isobutyl ketone (MIBK); esters, including methyl acetate, ethyl formate, ethyl acetate, propyl acetate, isopropyl acetate, isobutyl acetate, and butyl acetate; carbonates, including ethylene carbonate and propylene carbonate; amides, including formamide, N,N-dimethylformamide (DMF), and N,N-dimethylacetamide; nitriles, including acetonitrile (ACN); sulfoxides, such as dimethyl sulfoxide (DMSO); sulfones, such sulfolane; nitro compounds, such as nitromethane and nitrobenzene; heterocycles, such as N-methyl pyrrolindone, 2-methyl tetrahydrofuran, tetrahydrofuran (THF), dioxane, and pyridine; carboxylic acids, such as acetic acid, trichloroacetic acid, and trifluoroacetic acid; phosphoramides, such as hexamethylphosphoramide; carbon sulfide; water; and mixtures thereof.

In one embodiment, the solvent for the contacting step to form the nitrite salt of 1,1-dimethylbiguanide provided herein is acetonitrile, acetone, methyl ethyl ketone, methyl isobutyl ketone, N,N-dimethylformamide, dimethylsulfoxide, a low alkanol (e.g., methanol, ethanol, n-propanol, isopropanol, sec-butanol, or 2-methoxyethanol), methyl acetate, ethyl acetate, ethyl formate, isopropyl acetate, isobutyl acetate, chloroform, dichloromethane, methyl tert-butyl ether, tetrahydrofuran, 1,4-dioxane, petroleum ether, hexanes, heptane, toluene, water, or a mixture thereof. In another embodiment, the solvent for the contacting step to form the nitrite salt of 1,1-dimethylbiguanide provided herein comprises a $C_{1-5}$ alkanol. In yet another embodiment, the solvent for the contacting step to form the nitrite salt of 1,1-dimethylbiguanide provided herein comprises methanol, ethanol, propanol, isopropanol, sec-butanol, 2-methoxyethanol, or a mixture thereof.

In certain embodiments, the contacting step to form the nitrite salt of 1,1-dimethylbiguanide provided herein is carried out at a temperature ranging from about −10 to about 150° C., from about 10 to about 110° C., or from about 20 to about 100° C.

In yet another embodiment, the processes provided herein each further comprise the step of crystallizing the nitrite salt of 1,1-dimethylbiguanide at a second predetermined temperature.

Suitable solvents for crystallization include, but are not limited to, hydrocarbons, including petroleum ether, pentane, hexane(s), heptane, octane, isooctane, cyclopentane, cyclohexane, methylcyclohexane, benzene, toluene, xylene, tetralin, and cumene; chlorinated hydrocarbons, including dichloromethane (DCM), 1,2-dichloroethane, 1,1-dichloroethene, 1,2-dichloroethene, chloroform, trichloroethane, trichloroethene, carbon tetrachloride, chlorobenzene, and trifluoromethylbenzene; alcohols, including methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, and ethyleneglycol; ethers, including diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, and anisole; ketones, including acetone, butanone, methyl ethyl ketone (MEK), methyl isopropyl ketone, methyl butyl ketone, and methyl isobutyl ketone (MIBK); esters, including methyl acetate, ethyl formate, ethyl acetate, propyl acetate, isopropyl acetate, isobutyl acetate, and butyl acetate; carbonates, including ethylene carbonate and propylene carbonate; amides, including formamide, N,N-dimethylformamide (DMF), and N,N-dimethylacetamide; nitriles, including acetonitrile (ACN); sulfoxides, such as dimethyl sulfoxide (DMSO); sulfones, such sulfolane; nitro compounds, such as nitromethane and nitrobenzene; heterocycles, such as N-methyl pyrrolindone, 2-methyl tetrahydrofuran, tetrahydrofuran (THF), dioxane, and pyridine; carboxylic acids, such as acetic acid, trichloroacetic acid, and trifluoroacetic acid; phosphoramides, such as hexamethylphosphoramide; carbon sulfide; water; and mixtures thereof.

In one embodiment, the solvent for crystallization is acetonitrile, acetone, methyl ethyl ketone, methyl isobutyl ketone, N,N-dimethylformamide, dimethylsulfoxide, a low alkanol (e.g., methanol, ethanol, n-propanol, isopropanol, sec-butanol, or 2-methoxyethanol), methyl acetate, ethyl acetate, ethyl formate, isopropyl acetate, isobutyl acetate, chloroform, dichloromethane, methyl tert-butyl ether, tetrahydrofuran, 1,4-dioxane, petroleum ether, hexanes, heptane, toluene, water, or a mixture thereof. In another embodiment, the solvent for crystallization comprises a $C_{1-5}$ alkanol. In yet another embodiment, the solvent for crystallization comprises methanol, ethanol, propanol, isopropanol, sec-butanol, 2-methoxyethanol, or a mixture thereof.

In certain embodiment, the crystallization is carried out using conventional methods, including, but not limited to, cooling, chilling, solvent evaporation, addition of an anti-solvent, or reverse addition to an anti-solvent. In certain embodiment, the crystallization is carried out at a temperature ranging from about −50 to about 100° C., from about −30 to about 50° C., or from about −10 to about 30° C. In certain embodiments, the process further comprises the step of seeding to accelerate crystallization. In certain embodiments, the process further comprises an isolation step, in which the solid formed is isolated by a conventional method, such as filtration and centrifugation, followed by washing with a solvent and then drying.

In certain embodiment, the crystallization is carried out by cooling a solution containing the nitrite salt of 1,1-dimethylbiguanide provided herein to or below room temperature, or by solvent evaporation. In certain embodiment, the crystallization is carried out by adding an anti-solvent to a solution containing the nitrite salt of 1,1-dimethylbiguanide provided herein, or by adding a solution containing the nitrite salt of 1,1-dimethylbiguanide provided herein to an anti-solvent.

Suitable anti-solvents include, but are not limited to, hydrocarbons, including petroleum ether, pentane, hexane(s), heptane, octane, isooctane, cyclopentane, cyclohexane, methylcyclohexane, benzene, toluene, xylene, tetralin, and cumene; chlorinated hydrocarbons, including dichloromethane, 1,2-dichloroethane, 1,1-dichloroethene, 1,2-dichloroethene, chloroform, trichloroethane, trichloroethene, carbon tetrachloride, chlorobenzene, and trifluoromethylbenzene; alcohols, including isopropanol, 1-propanol, 1-butanol, 2-butanol, t-butanol, 3-methyl-1-butanol, 1-pentanol, 2-ethoxyethanol, and ethyleneglycol; ethers, including diethyl ether, diisopropyl ether, methyl t-butyl ether, diphenyl ether, 1,2-dimethoxyethane, bi(2-methoxyethyl)ether, 1,1-dimethoxymethane, 2,2-dimethoxypropane, and anisole; ketones, including butanone, methyl isopropyl ketone, methyl butyl ketone, and methyl isobutyl ketone; esters, including methyl acetate, ethyl formate, ethyl acetate, propyl acetate, isopropyl acetate, isobutyl acetate, and butyl acetate; carbonates, including ethylene carbonate and propylene carbonate; nitro compounds, including nitromethane and nitrobenzene; heterocycles; carbon sulfide; water; and mixtures thereof.

When two solvents are used as a solvent/anti-solvent pair, the nitrite salt of 1,1-dimethylbiguanide has a higher solubility in the solvent than in the anti-solvent. Optionally, the solvent and the anti-solvent in a solvent/anti-solvent pair are at least partially miscible.

Pharmaceutical Compositions

In one embodiment, provided herein is a pharmaceutical composition comprising a nitrite salt of 1,1-dimethylbiguanide provided herein, e.g., a solid nitrite salt or an isolated nitrite salt of 1,1-dimethylbiguanide, or an isotopic variant thereof; or a pharmaceutically acceptable hydrate or solvate thereof; and one or more pharmaceutically acceptable excipients.

The pharmaceutical compositions provided herein can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd Edition, Rathbone et al., Eds., Marcel Dekker, Inc.: New York, N.Y., 2008).

In one embodiment, the pharmaceutical compositions provided herein are formulated in a dosage form for oral administration, which comprise a nitrite salt of 1,1-dimethylbiguanide provided herein, e.g., a solid nitrite salt or an isolated nitrite salt of 1,1-dimethylbiguanide, or an isotopic variant thereof; or a pharmaceutically acceptable hydrate or solvate thereof; and one or more pharmaceutically acceptable excipients.

In one embodiment, the oral pharmaceutical composition comprises a nitrite salt of 1,1-dimethylbiguanide provided herein, e.g., a solid nitrite salt or an isolated nitrite salt of 1,1-dimethylbiguanide, or an isotopic variant thereof; or a pharmaceutically acceptable hydrate or solvate thereof; and one or more pharmaceutically acceptable excipients, each of which is independently selected from candellila wax, cellulose acetate, crospovidone or povidone, dibutyl sebacate, ethylcellulose, glyceryl behenate, hypromellose, magnesium stearate, microcrystalline cellulose, polyethylene glycol (e.g., PEG 400 or PEG 8000), polyvinyl alcohol, polysorbate (e.g., polysorbate 80), sodium carboxymethyl cellulose, sodium dioxide, sodium lauryl sulfate, synthetic black iron oxides, titanium dioxide, triacetin, hydrochloric acid, potassium bicarbonate, saccharin calcium, xylitol, water, and cherry flavor.

In another embodiment, the oral pharmaceutical composition comprises a nitrite salt of 1,1-dimethylbiguanide provided herein, e.g., a solid nitrite salt or an isolated nitrite salt of 1,1-dimethylbiguanide, or an isotopic variant thereof; or a pharmaceutically acceptable hydrate or solvate thereof; and one, two, or more pharmaceutically acceptable excipients, each of which is independently selected from candellila wax, cellulose acetate, corn starch, crospovidone or povidone, dibutyl sebacate, ethylcellulose, glyceryl behenate, hypromellose, magnesium stearate, microcrystalline cellulose, polyethylene glycol, polyvinyl alcohol, polysorbate, sodium carboxymethyl cellulose, sodium dioxide, sodium lauryl sulfate, synthetic black iron oxides, titanium dioxide, and triacetin.

In one embodiment, the oral pharmaceutical composition is a tablet. In another embodiment, the oral pharmaceutical composition is an extended-release tablet. In yet another embodiment, the oral pharmaceutical composition is a coated tablet.

In another embodiment, the pharmaceutical compositions provided herein are formulated in a dosage form for parenteral administration, which comprise a nitrite salt of 1,1-dimethylbiguanide provided herein, e.g., a solid nitrite salt or an isolated nitrite salt of 1,1-dimethylbiguanide, or an isotopic variant thereof; or a pharmaceutically acceptable hydrate or solvate thereof; and one or more pharmaceutically acceptable excipients. In one embodiment, the pharmaceutical compositions provided herein are formulated in a dosage form for intravenous administration. In another embodiment, the pharmaceutical compositions provided herein are formulated in a dosage form for intramuscular administration. In yet another embodiment, the pharmaceutical compositions provided herein are formulated in a dosage form for subcutaneous administration.

In yet another embodiment, the pharmaceutical compositions provided herein are formulated in a dosage form for topical administration, which comprise a nitrite salt of 1,1-dimethylbiguanide provided herein, e.g., a solid nitrite salt or an isolated nitrite salt of 1,1-dimethylbiguanide, or an isotopic variant thereof; or a pharmaceutically acceptable hydrate or solvate thereof; and one or more pharmaceutically acceptable excipients.

In yet another embodiment, the pharmaceutical compositions provided herein each independently further comprise a second 1,1-dimethylbiguanide salt. In certain embodiments, the second 1,1-dimethylbiguanide salt is a hydrochloric acid, hydrobromic acid, or sulfuric acid salt of 1,1-dimethylbiguanide. In certain embodiments, the second 1,1-dimethylbiguanide salt is a 1,1-dimethylbiguanide hydrochloric acid salt. In certain embodiments, the second 1,1-dimethylbiguanide salt is 1,1-dimethylbiguanide monohydrochloride. In certain embodiments, the second 1,1-dimethylbiguanide salt is 1,1-dimethylbiguanide dihydrochloride.

In yet another embodiment, the pharmaceutical compositions provided herein each independently further comprise a second nitrite salt. In certain embodiments, the second nitrite salt is sodium nitrite. In certain embodiments, the second nitrite salt is potassium nitrite. In certain embodiments, the second nitrite salt is silver nitrite. In certain embodiments, the pharmaceutical compositions provided herein comprise in each unit-dosage form the second nitrite salt in the amount ranging from about 1 to about 100 mg. In certain embodiments, the pharmaceutical compositions provided herein comprise in each unit-dosage form the second nitrite salt in the amount of about 1, about 5, about 10, about 20, about 30, about 40, about 50, about 60, about 70, about 80, about 90, or about 100 mg.

In still another embodiment, the pharmaceutical compositions provided herein each independently further comprise an additional therapeutic agent. In certain embodiments, the additional therapeutic agent is an additional antidiabetic agent. In certain embodiments, the additional antidiabetic agent is an alpha-glucosidase inhibitor, an amylin analogue, a dipeptidyl peptidase 4 inhibitor, an incretin mimetic, a meglitinide, a non-sulfonylurea, a SGLT-2 inhibitor, a sulfonyl urea, a thiazolidinedione, or a combination thereof. In certain embodiments, the additional antidiabetic agent is acarbose, albiglutide, alogliptin, canagliflozin, ciglitazone, chlorpropamide, dapagliflozin, darglitazone, dulaglutide, empagliflozin, englitazone, exenatide, glimepiride, gliclazide, glipizide, glyburide, linagliptin, liraglutide, lixisenatide, lobeglitazone, miglitol, nateglinide, netoglitazone, pioglitazone, pramlintide, repaglinide, rosiglitazone, reviglitazone, saxagliptin, sitagliptin, tolbutamide, tolazamide, troglitazone, or a combination thereof.

In certain embodiments, the pharmaceutical compositions provided herein are provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

In certain embodiments, the pharmaceutical compositions provided herein comprise in each unit-dosage form the nitrite salt of 1,1-dimethylbiguanide provided herein in the amount ranging from about 10 to about 10,000 mg. In certain embodiments, the pharmaceutical compositions provided herein comprise in each unit-dosage form the nitrite salt of 1,1-dimethylbiguanide provided herein in the amount of about 100, about 200, about 300, about 400, about 500, about 550, about 600, about 650, about 700, about 750, about 800, about 850, about 900, about 950, about 1,000, about 1,050, about 1,100, about 1,150, about 1,200, about 1,250, about 1,300, about 1,350, about 1,400, about 1,450, and about 1,500 mg.

In certain embodiments, the pharmaceutical compositions provided herein comprise in each unit-dosage form the nitrite salt of 1,1-dimethylbiguanide provided herein in the amount ranging from about 1 to about 100, about 1 to about 50, from about 2 to about 20, or from about 2 to about 10 mg. In certain embodiments, the pharmaceutical compositions provided herein comprise in each unit-dosage form the nitrite salt of 1,1-dimethylbiguanide provided herein in the amount of about 1, about 2, about 3, about 4, about 5, about 6, about 7, about 8, about 9, about 10, about 11, about 12, about 13, about 14, about 15, about 16, about 17, about 18, about 19, or about 20 mg.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; algins; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained-, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber, epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as 1-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided herein is a method of treating, preventing, or ameliorating a disease associated with and/or caused by an abnormal blood glucose level in a subject, comprising administering to the subject a therapeutically effective amount of a nitrite salt of 1,1-dimethylbiguanide provided herein, e.g., a solid nitrite salt or an isolated nitrite salt of 1,1-dimethylbiguanide, or an isotopic variant thereof; or a pharmaceutically acceptable hydrate or solvate thereof.

In one embodiment, the disease associated with and/or caused by an abnormal blood glucose level is a disease associated with and/or caused by hyperglycemia. In another embodiment, the disease associated with and/or caused by an abnormal blood glucose level is a disease associated with and/or caused by a diabetes. In yet another embodiment, the disease associated with and/or caused by an abnormal blood glucose level is a disease associated with and/or caused by type 1 diabetes. In yet another embodiment, the disease associated with and/or caused by an abnormal blood glucose level is a disease associated with and/or caused by type 2 diabetes. In still another embodiment, the disease associated with and/or caused by an abnormal blood glucose level is a diabetes. In one embodiment, the diabetes is type 1 diabetes. In another embodiment, the diabetes is type 2 diabetes.

In certain embodiments, the disease associated with and/or caused by an abnormal blood glucose level is a cardiovascular disease, diabetic neuropathy, diabetic nephropathy, diabetic retinopathy, diabetes, dyslipidemia, elevated plasma insulin concentration, hepatic steatosis, hyperglycemia, hyperlipidemia, hypertension, impaired glucose tolerance, insulin resistance, lipodystrophy, metabolic syndrome, obesity, polycystic ovary syndrome, or pulmonary hypertension (PH).

In certain embodiments, the disease associated with and/or caused by an abnormal blood glucose level is a cardiovascular disease. In certain embodiments, the cardiovascular disease is acute myocardial infarction, aortic aneurysms, atherosclerosis, atherosclerosis, atrial fibrillation, atrial flutter, cardiomyopathy, carditis, cerebrovascular disease, chest pain (angina), congenital heart disease, coronary artery disease, endocarditis, haemorrhagic stroke, heart arrhythmia, heart attack, heart failure, heart failure with preserved ejection fraction, hypertensive heart disease, ischemic heart disease, ischaemic stroke, left ventricular dysfunction, myocardial fibrosis, myocardial infarction (heart attack), myocardial ischemia, myocarditis, peripheral artery disease, peripheral vascular disease, pulmonary hypertension associated with heart failure with preserved ejection fraction, rheumatic heart disease, stroke, valvular heart disease, or venous thrombosis. In certain embodiments, the cardiovascular disease is heart failure. In certain embodiments, the cardiovascular disease is left ventricular dysfunction. In certain embodiments, the cardiovascular disease is heart failure with preserved ejection fraction (HFpEF). In certain embodiments, the cardiovascular disease is pulmonary hypertension associated with heart failure with preserved ejection fraction (PH-HFpEF). In certain embodiments, the disease associated with and/or caused by an abnormal blood glucose level is diabetic nephrophathy. In certain embodiments, the diabetic nephrophathy is kidney failure or irreversible end-stage kidney disease. In certain embodiments, the disease associated with and/or caused by an abnormal blood glucose level is diabetic neuropathy. In certain embodiments, the disease associated with and/or caused by an abnormal blood glucose level is diabetic retinopathy. In certain embodiments, the diabetic retinopathy is cataracts or glaucoma.

In certain embodiments, the disease associated with and/or caused by an abnormal blood glucose level is hepatic steatosis. In certain embodiments, the disease associated with and/or caused by an abnormal blood glucose level is hypertension. In certain embodiments, the disease associated with and/or caused by an abnormal blood glucose level is metabolic syndrome. In certain embodiments, the disease associated with and/or caused by an abnormal blood glucose level is obesity. In certain embodiments, the disease associated with and/or caused by an abnormal blood glucose level is polycystic ovary syndrome. In certain embodiments, the disease associated with and/or caused by an abnormal blood glucose level is hypertension. In certain embodiments, the disease associated with and/or caused by an abnormal blood glucose level is pulmonary hypertension.

In certain embodiments, the disease associated with and/or caused by an abnormal blood glucose level is type 2 diabetes. In certain embodiments, the disease associated with and/or caused by an abnormal blood glucose level is gestational diabetes. In certain embodiments, the disease associated with and/or caused by an abnormal blood glucose level is insulin resistance.

Depending on the disease to be treated and the subject's condition, the nitrite salt of 1,1-dimethylbiguanide provided herein may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration and may be formulated, alone or together, in suitable dosage unit with pharmaceutically acceptable carriers, adjuvants and vehicles appropriate for each route of administration. Also provided is administration of the nitrite salt of 1,1-dimethylbiguanide provided herein in a depot formulation, in which the active ingredient is released over a predefined time period.

In the treatment, prevention, or amelioration of one or more symptoms of the disease associated with and/or caused by an abnormal blood glucose level, an appropriate dosage level the nitrite salt of 1,1-dimethylbiguanide provided herein generally is ranging from about 10 to about 5,000, from about 100 to about 3,000, or from about 200 to about 2,500 mg per day (mg/day), which may be administered in single or multiple doses. Within this range the dosage may be about 500, about 600, about 700, about 800, about 900, about 1,000, about 1,100, about 1,200, about 1,300, about 1,400, about 1,500, about 1,600, about 1,700, about 1,800, about 1,900, about 2,000, about 2,100, about 2,200, about 2,300, about 2,400, or about 2,500 mg/day.

For oral administration, the pharmaceutical compositions can be provided in the form of tablets containing from 10 to 10,000 mg of the nitrite salt of 1,1-dimethyl-biguanide provided herein, particularly about 100, about 200, about 300, about 400, about 500, about 550, about 600, about 650, about 700, about 750, about 800, about 850, about 900, about 950, about 1,000, about 1,050, about 1,100, about 1,150, about 1,200, about 1,250, about 1,300, about 1,350, about 1,400, about 1,450, and about 1,500 mg of the active ingredient for the symptomatic adjustment of the dosage to the patient to be treated. The compositions may be administered on a regimen of 1 to 4 times per day, including once, twice, three times, and four times per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In another embodiment, provided herein is a method of treating, preventing, or ameliorating one or more symptoms of pulmonary hypertension in a subject, comprising administering to the subject a therapeutically effective amount of a nitrite salt of 1,1-dimethylbiguanide provided herein, e.g., a solid nitrite salt or an isolated nitrite salt of 1,1-dimethylbiguanide, or an isotopic variant thereof; or a pharmaceutically acceptable hydrate or solvate thereof.

In yet another embodiment, provided herein is a method of treating, preventing, or ameliorating one or more symptoms of a cardiovascular disease in a subject, comprising administering to the subject a therapeutically effective amount of a nitrite salt of 1,1-dimethylbiguanide provided herein, e.g., a solid nitrite salt or an isolated nitrite salt of 1,1-dimethylbiguanide, or an isotopic variant thereof; or a pharmaceutically acceptable hydrate or solvate thereof.

In certain embodiments, the cardiovascular disease is acute myocardial infarction, aortic aneurysms, atherosclerosis, atherosclerosis, atrial fibrillation, atrial flutter, cardiomyopathy, carditis, cerebrovascular disease, chest pain (angina), congenital heart disease, coronary artery disease, endocarditis, haemorrhagic stroke, heart arrhythmia, heart attack, heart failure, heart failure with preserved ejection fraction, hypertensive heart disease, ischemic heart disease, ischaemic stroke, left ventricular dysfunction, myocardial fibrosis, myocardial infarction (heart attack), myocardial ischemia, myocarditis, peripheral artery disease, peripheral vascular disease, pulmonary hypertension associated with heart failure with preserved ejection fraction, rheumatic heart disease, stroke, valvular heart disease, or venous thrombosis. In certain embodiments, the cardiovascular disease is heart failure. In certain embodiments, the cardiovascular disease is heart failure with preserved ejection fraction (HFpEF). In certain embodiments, the cardiovascular disease is pulmonary hypertension associated with heart failure with preserved ejection fraction (PH-HFpEF).

In certain embodiments, in the treatment, prevention, or amelioration of one or more symptoms of the cardiovascular disease, an appropriate dosage level the nitrite salt of 1,1-dimethylbiguanide provided herein generally is ranging from about 1 to about 5,000, about 1 to about 2,000, from about 2 to about 1,000, or from about 2 to about 500 mg per day (mg/day), which may be administered in single or multiple doses. Within this range the dosage may be about 500, about 600, about 700, about 800, about 900, about 1,000, about 1,100, about 1,200, about 1,300, about 1,400, about 1,500, about 1,600, about 1,700, about 1,800, about 1,900, about 2,000, about 2,100, about 2,200, about 2,300, about 2,400, or about 2,500 mg/day.

In certain embodiments, in the treatment, prevention, or amelioration of one or more symptoms of the cardiovascular disease, an appropriate dosage level the nitrite salt of 1,1-dimethylbiguanide provided herein generally is ranging from about 1 to about 100, about 1 to about 50, from about 2 to about 20, or from about 2 to about 10 mg/day, which may be administered in single or multiple doses. Within this range the dosage may be about 1, about 2, about 3, about 4, about 5, about 6, about 7, about 8, about 9, about 10, about 11, about 12, about 13, about 14, about 15, about 16, about 17, about 18, about 19, or about 20 mg/day.

For oral administration, the pharmaceutical compositions can be provided in the form of tablets containing from 1 to 100 mg of the nitrite salt of 1,1-dimethyl-biguanide provided herein, particularly about 1, about 2, about 3, about 4, about 5, about 6, about 7, about 8, about 9, about 10, about 11, about 12, about 13, about 14, about 15, about 16, about 17, about 18, about 19, or about 20 mg of the active ingredient for the symptomatic adjustment of the dosage to the patient to be treated. The compositions may be administered on a regimen of 1 to 4 times per day, including once, twice, three times, and four times per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In yet another embodiment, provided herein is a method of reducing the blood glucose level in a subject, comprising administering to the subject a therapeutically effective amount of a nitrite salt of 1,1-dimethylbiguanide provided herein, e.g., a solid nitrite salt or an isolated nitrite salt of 1,1-dimethylbiguanide, or an isotopic variant thereof or a pharmaceutically acceptable hydrate or solvate thereof.

The nitrite salt of 1,1-dimethylbiguanide provided herein may also be combined or used in combination with an additional therapeutic agent useful in the treatment, prevention, or amelioration of one or more symptoms of the diseases or conditions for which the nitrite salt of 1,1-dimethylbiguanide provided herein are useful. In one embodiment, the additional therapeutic agent is an antidiabetic agent. In certain embodiments, the additional antidiabetic agent is an alpha-glucosidase inhibitor, an amylin analogue, a dipeptidyl peptidase 4 inhibitor, an incretin mimetic, a meglitinide, a non-sulfonylurea, a SGLT-2 inhibitor, a sulfonyl urea, or a thiazolidinedione, or a combination thereof. In certain embodiments, the additional antidiabetic agent is acarbose, albiglutide, alogliptin, canagliflozin, ciglitazone, chlorpropamide, dapagliflozin, darglitazone, dulaglutide, empagliflozin, englitazone, exenatide, glimepiride, gliclazide, glipizide, glyburide, linagliptin, liraglutide, lixisenatide, lobeglitazone, miglitol, nateglinide, netoglitazone, pioglitazone, pramlintide, repaglinide, rosiglitazone, reviglitazone, saxagliptin, sitagliptin, tolbutamide, tolazamide, troglitazone, or a combination thereof.

Such an additional therapeutic agent may be administered, by a route and in an amount commonly used therefor, simultaneously or sequentially with the nitrite salt of 1,1-dimethylbiguanide provided herein. When a nitrite salt of 1,1-dimethylbiguanide provided herein is used contemporaneously with one or more other drugs, a pharmaceutical composition containing such other drugs in addition to the nitrite salt of 1,1-dimethylbiguanide provided herein may be utilized, but is not required. Accordingly, the pharmaceutical compositions provided herein include those that also contain one or more other active ingredients or therapeutic agents, in addition to the nitrite salt of 1,1-dimethylbiguanide provided herein.

In certain embodiments, provided herein also are kits which, when used by the medical practitioner, can simplify the administration of appropriate amounts of active ingredients to a subject. In certain embodiments, the kit provided herein includes a container and a dosage form of a nitrite salt of 1,1-dimethylbiguanide provided herein. In certain embodiments, the kit includes a container comprising a dosage form of a nitrite salt of 1,1-dimethylbiguanide provided herein, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

Example 1

Preparation of
1-(amino(dimethylamino)methylidene]guanidine
nitrite using sodium nitrite Sodium nitrite (0.417 g, 0.006 mol) was added to a solution of 1-(amino(dimethylamino)methylidene]guanidine hydrochloride (1.00 g, 0.006 mol) in water (10 mL). After stirring at room temperature for 2 hours, 10 mL ethanol was added, and the reaction mixture was concentrated under vacuum with warming to 40° C. to remove all solvents. Ethanol (20 mL) was added to the resulting solid, and the mixture was vortexed for 5 minutes then filtered. The filtrate was concentrated under vacuum to afford the title compound as a mixture of 1-(amino(dimethylamino)methylidene]guanidine nitrite and residual NaCl (0.432 g of the mixture, 35% yield of 1-(amino(dimethylamino)methylidene]-guanidine nitrite). $^1$H NMR (d-DMSO) 7.20 (s, 2H), 6.71 (s, 4H), 2.92 (s, 6H). Elemental analysis: C, 24.29%, H, 5.73%, N, 40.82%.

Example 2

Preparation of 1-(amino(dimethylamino)methylidene]guanidine nitrite using sodium nitrite Sodium nitrite (0.417 g, 0.006 mol) was added to a solution of 1-(amino(dimethylamino)methylidene]guanidine hydrochloride (1.00 g, 0.006 mol) in water (10 mL). After stirring at room temperature for 1 day, 10 mL ethanol was added, and the reaction mixture was concentrated under vacuum with warming to 40° C. to remove all solvents. Ethanol (20 mL) was added to the resulting solid, and the mixture was vortexed for 5 minutes then filtered. The filtrate was concentrated under vacuum. To the resulting solid was added 6 mL of a solution of acetone and ethanol (1:1). After vortexing 3 minutes, the mixture was filtered and the filtrate was set aside. The remaining solid was vortexed 3 minutes with an additional 6 mL of the acetone and ethanol (1:1) solution. After filtration, the filtrates were combined and concentrated under vacuum to afford the title compound as a mixture of 1-(amino(dimethylamino)methylidene]guanidine nitrite hemihydrate and residual NaCl (0.153 g of the mixture, 14% yield of 1-(amino(dimethylamino)methylidene]guanidine nitrite hemihydrate). Elemental analysis: C, 23.38%, H, 5.82%, N, 42.47%, Cl, 2.75%.

Example 3

Preparation of 1-(amino(dimethylamino)methylidene]guanidine nitrite using silver nitrite An aqueous solution of silver nitrite (1 eq.) is added to a solution of 1-(amino(dimethylamino)methylidene]guanidine hydrochloride (1 eq.) in water. After removing the precipitation by filtration, the solution is concentrated to yield 1-(amino(dimethylamino)methylidene]guanidine nitrite.

Example 4

Preparation of 1-(amino(dimethylamino)methylidene]guanidine nitrite using potassium nitrite Metformin hydrochloride (12.0 g) was supended in DMF (240 mL). Potassium nitrite (12.8 g, 2 eq.) was added and the reaction mixture was stirred to room temperature for 2.5 hours. After the reaction mixture was filtered, ethyl acetate (130 mL) was added to the resulting filtrate until a turbid solution was formed. Potassium nitritie (50 mg) was added, stirred for 3 hours, and filtered. Additional ethyl acetate (160 mL) was added to the resulting filtrate, followed by the addition of metformin nitrite (50 mg). The mixture was stirred for 10 minutes at room temperature, during which time a significant amount of solid formed. Additional ethyl actate (200 mL) was added and the mixture was stirred overnight at room temperature. The solid was filtered and dried under vacuum to yield metformin nitrite (11.08 g, 81% yield). $^1$H NMR (DMSO-$d_6$) δ 7.19 (s, 2H), 6.71 (s, 4H), 2.90 (s, 6H).

Example 5

Preparation of 1-(amino(dimethylamino)methylidene]guanidine nitrite using silver nitrite To a solution of metformin hydrochloride (1.048 g) in methanol (35 mL) was added $AgNO_2$ (1 eq.) at room temperature. The reaction mixture was stirred at room temperature for 5 hours. After filtration, the resulting filtrate was concentrated to yield metformin nitrite (1.098 g, 98% yield). $^1$H NMR (DMSO-$d_6$) δ 7.19 (s, 2H), 6.71 (s, 4H), 2.90 (s, 6H).

The examples set forth above are provided to give those of ordinary skill in the art with a complete disclosure and description of how to make and use the embodiments, and are not intended to limit the scope of the disclosure. Modifications of the above-described modes for carrying out the disclosure that are obvious to persons of skill in the art are intended to be within the scope of the following claims. All publications, patents, and patent applications cited in this specification are incorporated herein by reference as if each such publication, patent, or patent application were specifically and individually indicated to be incorporated herein by reference.

What is claimed is:

1. A solid nitrite salt of 1,1-dimethylbiguanide, or an isotopic variant thereof; or a pharmaceutically acceptable hydrate or solvate thereof.

2. The nitrite salt of claim 1, wherein the nitrite salt is 1,1-dimethylbiguanide mononitrite, or an isotopic variant thereof or a pharmaceutically acceptable hydrate or solvate thereof.

3. The nitrite salt of claim 1, wherein the nitrite salt is 1,1-dimethylbiguanide dinitrite, or an isotopic variant thereof; or a pharmaceutically acceptable hydrate or solvate thereof.

4. The nitrite salt of claim 1, wherein the nitrite salt is in a crystalline form.

5. An isolated nitrite salt of 1,1-dimethylbiguanide, or an isotopic variant thereof or a pharmaceutically acceptable hydrate or solvate thereof.

6. A composition comprising the nitrite salt of claim 1, or an isotopic variant thereof; or a pharmaceutically acceptable hydrate or solvate thereof; and a metal nitrite.

7. The composition of claim 6, comprising no less than about 90% of the nitrite salt of claim 1, or the isotopic variant thereof; or the pharmaceutically hydrate or solvate thereof.

8. The composition of claim 6, comprising no greater than about 10% of the metal nitrite.

9. A pharmaceutical composition comprising the nitrite salt of claim 1, or an isotopic variant thereof; or a pharmaceutically acceptable hydrate or solvate thereof; and a pharmaceutically acceptable excipient.

10. The pharmaceutical composition of claim 9, wherein the pharmaceutical composition is formulated for single dose administration.

11. The pharmaceutical composition of claim 9, wherein the pharmaceutical composition is formulated as oral, parenteral, or intravenous dosage form.

12. The pharmaceutical composition of claim 11, wherein the pharmaceutical composition is formulated as oral dosage form.

13. The pharmaceutical composition of claim 12, wherein the oral dosage form is a tablet or capsule.

14. The pharmaceutical composition of claim 12, wherein the oral dosage form is a tablet.

15. The pharmaceutical composition of claim 9, wherein the pharmaceutically acceptable excipient is selected from candellila wax, cellulose acetate, corn starch, crospovidone or povidone, dibutyl sebacate, ethylcellulose, glyceryl behenate, hypromellose, magnesium stearate, microcrystalline cellulose, polyethylene glycol, polyvinyl alcohol, polysorbate, sodium carboxymethyl cellulose, sodium dioxide, sodium lauryl sulfate, synthetic black iron oxides, titanium dioxide, triacetin, and two or more combinations thereof.

16. The pharmaceutical composition of claim 9, further comprising a second 1,1-dimethylbiguanide salt.

17. The pharmaceutical composition of claim 16, wherein the second 1,1-dimethylbiguanide salt is a hydrochloric acid, hydrobromic acid, or sulfuric acid salt of 1,1-dimethylbiguanide.

18. The pharmaceutical composition of claim 16, wherein the second 1,1-dimethylbiguanide salt is 1,1-dimethylbiguanide monohydrochloride.

19. The pharmaceutical composition of claim 9, further comprising a second nitrite salt.

20. The pharmaceutical composition of claim 19, wherein the second nitrite salt is sodium nitrite, potassium nitrite, or silver nitrite.

21. The pharmaceutical composition of claim 19, wherein the pharmaceutical composition comprises the second nitrite salt in an amount ranging from about 1 to about 100 mg.

22. The pharmaceutical composition of claim 9, further comprising an additional therapeutic agent.

23. The pharmaceutical composition of claim 22, wherein the additional therapeutic agent is an additional antidiabetic agent.

24. The pharmaceutical composition of claim 23, wherein the additional antidiabetic agent is an alpha-glucosidase inhibitor, an amylin analogue, a dipeptidyl peptidase 4 inhibitor, an incretin mimetic, a meglitinide, a non-sulfonylurea, a SGLT-2 inhibitor, a sulfonyl urea, or a thiazolidinedione, or a combination thereof.

25. The pharmaceutical composition of claim 24, wherein the additional antidiabetic agent is acarbose, albiglutide, alogliptin, canagliflozin, ciglitazone, chlorpropamide, dapagliflozin, darglitazone, dulaglutide, empagliflozin, englitazone, exenatide, glimepiride, gliclazide, glipizide, glyburide, linagliptin, liraglutide, lixisenatide, lobeglitazone, miglitol, nateglinide, netoglitazone, pioglitazone, pramlintide, repaglinide, rosiglitazone, reviglitazone, saxagliptin, sitagliptin, tolbutamide, tolazamide, troglitazone, or a combination thereof.

26. The pharmaceutical composition of claim 9, wherein the pharmaceutical composition comprises from about 1 to about 10,000 mg of the nitrite salt of 1,1-dimethylbiguanide, or an isotopic variant thereof or a pharmaceutically acceptable hydrate or solvate thereof and a pharmaceutically acceptable excipient.

27. The pharmaceutical composition of claim 26, wherein the pharmaceutical composition comprises about 500, about 550, about 600, about 650, about 700, about 750, about 800, about 850, about 900, about 950, about 1,000, about 1,050, about 1,100, about 1,150, about 1,200, about 1,250, about 1,300, about 1,350, about 1,400, about 1,450, or about 1,500 mg of the nitrite salt of 1,1-dimethylbiguanide, or an isotopic variant thereof; or a pharmaceutically acceptable hydrate or solvate thereof; and a pharmaceutically acceptable excipient.

28. The pharmaceutical composition of claim 26, wherein the pharmaceutical composition comprises about 1, about 2, about 3, about 4, about 5, about 6, about 7, about 8, about 9, about 10, about 11, about 12, about 13, about 14, about 15, about 16, about 17, about 18, about 19, or about 20 mg of the nitrite salt of 1,1-dimethylbiguanide, or an isotopic variant thereof; or a pharmaceutically acceptable hydrate or solvate thereof; and a pharmaceutically acceptable excipient.

29. The pharmaceutical composition of claim 9, wherein the pharmaceutical composition is a coated tablet.

30. The pharmaceutical composition of claim 9, wherein the pharmaceutical composition is an extended-release tablet.

* * * * *